(12) United States Patent
Richards et al.

(10) Patent No.: US 8,623,389 B2
(45) Date of Patent: Jan. 7, 2014

(54) FORMULATIONS

(75) Inventors: Jonathan Mark Richards, Aigues-Vives (FR); Kirsty Jane Williams, Bracknell (GB)

(73) Assignee: Syngenta Limited (GB)

( * ) Notice: Subject to any disclaimer, the term of this patent is extended or adjusted under 35 U.S.C. 154(b) by 634 days.

(21) Appl. No.: 12/667,826

(22) PCT Filed: Jun. 9, 2008

(86) PCT No.: PCT/GB2008/001983
§ 371 (c)(1),
(2), (4) Date: Sep. 17, 2010

(87) PCT Pub. No.: WO2009/004281
PCT Pub. Date: Jan. 8, 2009

(65) Prior Publication Data
US 2010/0331187 A1    Dec. 30, 2010

(30) Foreign Application Priority Data
Jul. 3, 2007   (GB) .................................. 0712884.6

(51) Int. Cl.
*A01N 25/00*   (2006.01)

(52) U.S. Cl.
USPC ........................................ 424/405; 504/116.1

(58) Field of Classification Search
None
See application file for complete search history.

(56) References Cited

U.S. PATENT DOCUMENTS 6,479,432 B1 * 11/2002 Sixl .............................. 504/103

FOREIGN PATENT DOCUMENTS

| EP | 0070702 | | 1/1983 |
| EP | 143099 | * | 9/1983 |
| EP | 0143099 | | 5/1985 |
| EP | 149459 | * | 7/1985 |
| EP | 0149459 | | 7/1985 |
| EP | 0789999 | | 8/1997 |
| GB | 2008949 | | 6/1979 |
| GB | 2082913 | | 3/1982 |
| WO | 0130156 | | 5/2001 |
| WO | 2005051082 | | 6/2005 |
| WO | 2006131227 | | 12/2006 |

* cited by examiner

*Primary Examiner* — Alton Pryor
(74) *Attorney, Agent, or Firm* — Brian D. McAlhaney

(57) ABSTRACT

The present invention relates to physically stable oil dispersions. It also relates to a method for activating bentones that are designed for use with a low polarity organic systems. It also relates to physically stable oil dispersions comprising said activated bentone.

6 Claims, No Drawings

FORMULATIONS

This application is a 371 of International Application No. PCT/GB2008/001983 filed Jun. 9, 2008, which claims priority to GB 0712884.6 filed Jul. 3, 2007, the contents of which are incorporated herein by reference.

The present invention relates to physically stable oil dispersions. It also relates to a method for activating bentones that are designed for use with low polarity organic systems. It also relates to physically stable oil dispersions comprising said activated bentones.

Numerous formulation types are used in the agrochemical industry. The choice of formulation type depends on various factors, including the physical properties of the active ingredient itself. Oil dispersions are particularly useful for formulations containing oil insoluble active ingredients. They are also useful formulations for the inclusion of adjuvants that are generally oil based such as certain foliar penetration enhancing compounds (for example hydrophobic oils and surfactants).

In the absence of an anti-settling system, oil dispersions are prone to sedimentation. One type of anti-settling system for organic systems uses organoclays, such as bentones, as additives for imparting suspension and rheology control. Organoclays are made from natural smectite, hectorite or montmorillonite clays. The organoclay is prepared by reacting hydrophilic clay such as smectite with quaternary ammonium compounds, so that it becomes organophilic, and therefore compatible with non-aqueous media.

Dry organoclay takes the form of agglomerated platelet stacks. In order to function as an anti-settling system with good gel strength, it is necessary to both disperse the organoclay and add a chemical activator. If the organoclay is not well dispersed or chemically activated the result is poor gel strength and hence poor physical stability of the product. The degree of activation of organoclay is closely correlated with clay gel strength and physical stability.

The molecular-scale detail of the process of "activation" of bentone organoclays is not fully understood. However, the manufacturers of bentone recommend various polar species as suitable activators of bentones, including propylene carbonate, aqueous methanol, ethanol and acetone. GB-2,067,407 describes a liquid formulation of bendiocarb suspended in oil stabilised using suspending agents such as organically modified clays. EP-149,459 describes fluid suspensions comprising herbicidal substituted ureas, and stabilisation of the suspensions using silicas, optionally in combination with organophilic bentonites. GB-2,008,949 describes a fungicide dispersed in a hydrocarbon medium together with organophilized clay and a cationic aliphatic amine surfactant. Although each of these references describes the use of emulsifiers in the formulations, none of them discloses how to activate an organoclay to achieve formulations of good physical stability.

There exists a need to improve existing anti-settling systems, for example for use in improving the physical stability, storage stability and/or thixotropic flow properties of oil dispersions and oil suspension concentrates. The term oil dispersion encompasses oil suspension concentrates and diluted forms of said concentrates.

Surprisingly, it has now been found that in some situations, bentone clays suitable for use with low polarity organic systems can be activated by certain emulsifiers instead of polar species. In these situations, activation by emulsifiers can result in anti-settling systems that have better physical stability and/or extended storage stability compared to activation using a polar species.

The present invention avoids the need for the traditional chemical activators (polar species such as propylene carbonate) recommended by the organoclay manufacturers. Since emulsifiers are often added to formulations anyway (see for example GB-2,067,407), the present invention provides activation of the organoclay through the use of existing formulation components. Accordingly, the invention provides additional benefits of reduced cost and simplicity of manufacture of oil dispersions.

According to the present invention, there is provided a method of activating an organoclay stabiliser, which organoclay stabiliser is suitable for use with a low polarity liquid, comprising mixing the organoclay stabiliser with an emulsifier selected from the group consisting of alkyl ethoxylates, alkyl ethoxylate phosphate esters, alkyl sulphates, alkyl ammonium salts and castor oil ethoxylates, under high shear conditions in the presence of a low polarity liquid. Details of organoclays that are suitable for use with a low polarity liquid can be found in the technical bulletin published by Rheox in March 1997, entitled "Rheological additives products and applications". The alkyl chain of the emulsifier may be any chain length, straight chain or branched, and substituted or unsubstituted. Suitably it is unsubstituted.

The terms "activation" and "activating" refer to the formation of a gel structure in the clay.

An organoclay stabiliser that is suitable for use with a low polarity liquid is an organically modified hectorite, smectite or montmorillonite clay. The clay must be organically modified to make it organophilic and suitable for use in organic media. Further, the organoclay stabiliser must be one that requires chemical activation to achieve good gel strength.

Any low polarity liquid may be used in the invention. For example the liquid may be a paraffinic or mineral oil. Suitable organic media include mineral spirits, mineral oils, aliphatic compounds, hexane, heptane and white spirit. Suitably the liquid is a mineral oil such as Sunspray™ 11N. In the context of this invention, a liquid is said to have a low polarity where its properties are similar to those of the liquids mentioned above. Conversely a liquid is not said to have a low polarity where its properties are similar to those of, for example, methylated rape seed oil, oleic acid, dipropylene glycol dibenzoate or Solvesso 200. Suitably, a low polarity oil is one that has a dielectric constant less than 2.5.

The organoclay stabiliser must be suitably dispersed throughout the organic liquid to give the required gel effect. Suitably dispersed means that the initial aggregates of clay particles are broken apart. This is usually achieved by use of high intensity mixing, such as that produced by a mixer of the rotor/stator type such as the L4R model from Silverson. High intensity mixing is associated with high shear. The person skilled in the art will be familiar with suitable equipment and processes to effect suitable dispersion at the desired scale. Typically, for the present invention, high shear will be achieved by mixing the organoclay stabiliser in the low polarity oil using an appropriate high-intensity mixer at a tip speed of greater than about 2.5 m/s in a laboratory, or scaled up appropriately for manufacture in larger quantities. In one embodiment of the present invention, the organoclay stabiliser is mixed with the emulsifier under high shear conditions equivalent to that produced by a Silverson LAR at a tip speed of at least 2.5 m/s.

Emulsifiers from various different classes have been found to activate bentone clays in accordance with the present invention.

Alkyl ethoxylates that may be used in the present invention have a carbon chain length of from 4 to 30, and from 1 to 20 ethylene oxide units. Suitably, the alkyl ethoxylate has a carbon chain length of from 10 to 20, and from 2 to 10 ethylene oxide units. More suitably, the alkyl ethoxylate has a carbon chain length of from 16 to 18, and from 5 to 6 ethylene oxide units (for example Emulsogen M™ from Clariant). The person skilled in the art would be able to readily select suitable alkyl ethoxylate molecules that are soluble in low polarity liquids.

Alkyl ethoxylate phosphate esters that may be used in the present invention have a carbon chain length of from 4 to 30, and from 1 to 20 ethylene oxide units. Suitably, the alkyl ethoxylate phosphate ester has a carbon chain length of from 8 to 20, and from 2 to 10 ethylene oxide units. More suitably, the alkyl ethoxylate phosphate ester has a carbon chain length of from 10 to 15, and from 5 to 7 ethylene oxide units. Most suitably, the alkyl ethoxylate phosphate ester has a carbon chain length of 13, and 6 ethylene oxide units (for example Rhodafac RD610™ from Rhodia). The alkyl ethoxylate phosphate ester may be a mixture of mono- and di-esterified phosphates.

Alkyl sulphates that may be used in the present invention have a carbon chain length of from 4 to 30. Suitably, the alkyl sulphate has a carbon chain length of from 8 to 20, more suitably from 10 to 15, and most suitably 12 (for example Empicol LZ™).

Alkyl ammonium salts that may be used in the present invention have a carbon chain length of from 4 to 30. Suitably, the alkyl ammonium salt has a carbon chain length of from 8 to 20, more suitably from 13 to 18, and most suitably 16 (for example Arquad 16-50™ from Akzo Nobel). The alkyl ammonium salt may have one or two carbon chains, and typically includes methyl groups to quaternise the nitrogen atom.

Castor oil ethoxylates that may be used in the present invention have from 1 to 50 ethylene oxide units. Suitably, the castor oil ethoxylate has from 10 to 45 ethylene oxide units. More suitably it has from 20 to 40 ethylene oxide units. More suitably it has from 32 to 38 ethylene oxide units. Most suitably, the castor oil ethoxylate has from 34 to 36 ethylene oxide units (for example Sunaptol CA350™ from Uniqema).

As is well known to the person skilled in the art, the ethylene oxide values described above are average values.

The present invention also includes mixtures of emulsifiers for activating the organoclay stabiliser. Suitably, at least one of the emulsifiers is selected from those described above. More suitably, more than one of the emulsifiers are selected from those described above. Most suitably, all of the emulsifiers are selected from those described above. In one embodiment, the present invention excludes the emulsifier isooctyl alcohol ethoxylated with 6 moles ethylene oxide when used in combination with methylthiophanate.

The amount of activation, and corresponding physical stability of the resulting oil dispersion, is related to the amount of emulsifier used in relation to the amount of organoclay stabiliser present. The ratio of emulsifier to organoclay is generally from about 10:1 to about 1:10 by weight. Suitably, the ratio of emulsifier to organoclay stabiliser is from about 10:1 to about 1:1 by weight. The most suitable ratio of emulsifier to organoclay stabiliser depends on the specific emulsifier and organoclay stabiliser used. For example, a suitable ratio for Emulsogen M™ to Bentone 38™ in mineral oil is about 7.5:1 by weight.

The present invention may also comprise adding a polar activator to the organoclay stabiliser. The addition of low levels of polar activator in conjunction with the present invention, may result in improved organoclay stabiliser activation and physical stability. The amount of polar activator is suitably less than that recommended by the organoclay manufacturer (which is, for example, 33% by weight of dry Bentone™ for propylene carbonate). The amount of polar activator can be up to 20% w/w compared to the organoclay stabiliser. For example, the amount of polar activator is suitably less than 10% w/w, suitably less than 5% w/w, more suitably less than 2% w/w, and more suitably less than 1% w/w compared to the organoclay stabiliser. Some emulsifiers include small amounts of polar species such as water. Therefore, the total amount of polar activator present is the sum of the polar activator that is added, and any polar species that are present in the emulsifiers.

The term polar activator refers to a molecule that is capable of activating the organoclay stabiliser so that it forms a gel structure. For example, those skilled in the art will be familiar with the use of polar activators such as methanol, propylene carbonate and water in this context.

The present invention optionally comprises adding a glycol ether. The presence of a glycol ether further improves physical stability of the oil dispersion. Any suitable glycol ether may be used. Particularly suitable is propylene glycol n-monobutyl ether (Arcosolv PnB™) The ratio of glycol ether to organoclay stabiliser is between 100:1 to 1:100 by weight. Suitably, it is from 10:1 to 1:10 w/w. More suitably, it is about 2:1 w/w. The glycol ether may be added in addition to or instead of the polar activator.

The rate at which activation of the organoclay stabiliser takes place is temperature dependent. If activation is conducted at temperatures below 15° C., a gel structure is not formed until the mixture is warmed back to about 15° C. or above. Therefore, activation suitably takes place at about 15° C. or above. The higher the temperature is, the faster it is that activation takes place. The faster the rate of activation, the better the gel structure that is formed, and better associated physical stability of the resulting oil dispersion. Therefore, activation suitably takes place at about room temperature (i.e. from 18 to 25° C.) or above. More suitably, activation takes place at about 45° C. or above. Most suitably, activation takes place at about 60° C. Suitably, activation takes place from about 60° C. to about 70° C. The use of elevated temperatures may bring about manufacturing benefits.

Any suitable organoclay stabiliser may be used in the present invention, as long as it can be used in a low polarity liquid. The organoclay manufacturers provide a guide as to which organoclays are suitable for use in different media types. The organoclay stabiliser used in the present invention may be selected from the group consisting of organically modified bentonite, hectorite and smectite clays, for example tetraalkyl ammonium bentonite (for example Bentone™ 34), tetraalkyl ammonium hectorite (for example Bentone™ 38), tetra(alkyl/aryl) ammonium bentonite (for example Bentone SD™-1, Bentone™ 52, Bentone™ 120, and Bentone™ 1000), alkylaryl ammonium hectorite (for example Bentone SD™-3). Suitably, the organoclay stabiliser is selected from the group consisting of tetraalkyl ammonium bentonite, tetraalkyl ammonium hectorite and tetra(alkyl/aryl) ammonium bentonite. Suitably, the organoclay stabiliser is tetraalkyl ammonium bentonite. Suitably, the organoclay stabiliser is tetraalkyl ammonium hectorite. Suitably, the organoclay stabiliser is tetra(alkyl/aryl) ammonium bentonite.

According to the present invention there is provided a physically stable oil dispersion comprising an organoclay stabiliser that is suitable for use with a low polarity liquid; an emulsifier selected from the group consisting of alkyl ethoxylates, alkyl ethoxylate phosphate esters, alkyl sulphates, alkyl ammonium salts, and castor oil ethoxylates; a low polarity liquid; and a solid component that is substantially insoluble in the low polarity liquid; wherein the organoclay stabiliser is activated by the method defined above. A substantially insoluble solid component suitably has a solubility in the low polarity liquid at 20° C. not greater than about 100 mg/l. More suitably, substantially insoluble solid components useful in the present invention have a solubility in the low polarity liquid at 20° C. not greater than about 25 mg/l.

According to the present invention, there is provided a physically stable oil dispersion comprising an organoclay stabiliser that is suitable for use with a low polarity liquid; an emulsifier selected from the group consisting of alkyl ethoxylates, alkyl ethoxylate phosphate esters, alkyl sulphates, alkyl ammonium salts, and castor oil ethoxylates; a low polarity liquid; and a solid component that is substantially insoluble in the low polarity liquid; wherein the oil dispersion contains less than 20% polar activator w/w compared to the organoclay stabiliser.

According to the present invention, there is provided a physically stable oil dispersion comprising an organoclay stabiliser that is suitable for use with a low polarity liquid; an emulsifier selected from the group consisting of alkyl ethoxylates, alkyl ethoxylate phosphate esters, alkyl sulphates, alkyl ammonium salts, and castor oil ethoxylates; a low polarity liquid; a glycol ether and a solid component that is substantially insoluble in the low polarity liquid.

The oil dispersion is considered to be physically stable if no syneresis or sedimentation of the formulation components is observed for a prolonged period of time. The longer it takes for syneresis or sedimentation to occur, the more physically stable is the oil dispersion. An oil dispersion is considered to be physically stable if little or no syneresis or sedimentation is observed after 10 days at room temperature (i.e. from 18 to 25° C.). This is typically characterised by the presence of a less than 5% by volume visually apparent clear layer at the surface of stored material. Suitably, the oil dispersion of the invention is physically stable for more than 1 month at room temperature. The same assessment of physical stability applies to the visibility of anti-settling systems according to the invention.

The physically stable oil dispersions may also contain some or all of the optional embodiments of the invention described above.

In one embodiment, the physically stable oil dispersion of the present invention does not include silica.

The present invention may be used in any product, application or industry in which an oil dispersion with good physical stability is desired, such as paints, agrochemicals, pharmaceuticals, cosmetics, industrial finishes, coatings and inks. The oil dispersion may contain one or more additional components that are suitable for the particular use. Typically where oil dispersions are desired, at least one of said additional components is a solid at 20° C. that is substantially insoluble in oil.

When the oil dispersion is for use in the agrochemical industry, the solid component is an oil insoluble pesticide, active ingredient, fertiliser or adjuvant. Any pesticides that are substantially insoluble in oil may be used in conjunction with the invention, including for example herbicides, insecticides, fungicides, plant growth regulators, acaricides, nematicides, molluscicides and the like. The oil dispersion may contain more than one pesticide, at least one of which is substantially oil insoluble.

The person skilled in the art is familiar with the particle sizes for use in dispersions. Suitably, the solid component has a particle size of from about 0.5 to about 50 µm. More suitably, the solid component has a particle size of from about 1 to about 10 µm. More suitably, the solid component has a particle size of from about 2 to about 5 µm.

The substantially oil insoluble pesticide is suitably selected from the group consisting of ALS inhibitors, for example sulfonylureas, sulfamylureas, sulfonamides, imidazolinones, pyrimidinyloxypyridinecarboxylic acid derivatives, or pyrimidyloxybenzoic acid derivatives; HPPD inhibitors, for example triketones; neonicotinoids; carbamates; avermectins; pyrethroids; bisamides; triazoles; mandelamides; and strobilurins. Other classes of pesticides that are suitable for formulating as oil dispersions, such as those which are substantially oil-insoluble solid materials at room temperature, will be clearly understood by those skilled in the art.

Particularly suitable are herbicides from the class of sulfonylureas. The sulfonylurea is suitably selected from the group consisting of amidosulfuron, bensulfuron-methyl, chlorimuron-ethyl, chlorsulfuron, cinosulfuron, cyclosulfamuron, ethemetsulfuron-methyl, ethoxysulfuron, flazasulfuron, flucetosulfuron, flupyrsulfuron, foramsulfuron, halosulfuron-methyl, imazosulfuron, iodosulfuron, isosulfuron-methyl, mesosulfuron-methyl, metsulfuron-methyl, nicosulfuron, oxasulfuron, primisulfuron-methyl, prosulfuron, pyrazosulfuron-ethyl, rimsulfuron, sulfometuron-methyl, sulfosulfuron, thifensulfuron-methyl, triasulfuron, tribenuron-methyl, trifloxysulfuron, triflusulfuron-methyl and tritosulfuron, and any salt thereof. Particularly suitable are trifloxysulfuron, nicosulfuron, and salts thereof.

Particularly suitable neonicotinoids are thiamethoxam, imidacloprid and thiacloprid. A particularly suitable carbamate is mancozeb. A particularly suitable pyrethroid is deltamethrin. Particularly suitable HPPD inhibitors are mesotrione, tembotrione, topramezone and a compound of formula I

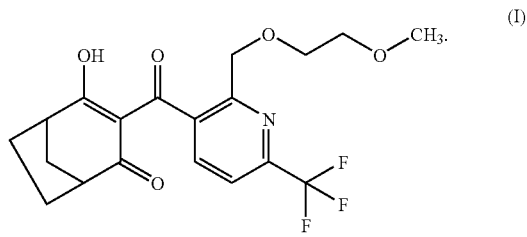 [SMILES: COCCOCc1nc(C(F)(F)F)ccc1C(=O)C1=C(O)C2CCC(C2)C1=O]

Particularly suitable triazoles are difenoconazole, fenbuconazole, penconazole, propiconazole and penoxsulam. A particularly suitable strobilurin is azoxystrobin.

The composition of the present invention may typically contain as little as about 0.5% to as much as about 95% or more by weight of each active ingredient. Suitably, the composition contains from 1% to 60% w/w of each active ingredient. In the case of sulfonylureas, the composition suitably contains from 1 to 10% w/w of each active ingredient.

According to the present invention, there is provided a method for making a physically stable oil dispersion, comprising providing an organoclay stabiliser that is suitable for use with a low polarity liquid; a low polarity liquid; an emulsifier selected from the group consisting of alkyl ethoxylates, alkyl ethoxylate phosphate esters, alkyl sulphates, alkyl ammonium salts and castor oil ethoxylates; and a solid component that is substantially insoluble in the low polarity liquid; and mixing the components under high shear conditions. Optional embodiments of the invention described above apply equally to this method.

The present invention further provides the use of an emulsifier selected from the group consisting of alkyl ethoxylates, alkyl ethoxylate phosphate esters, alkyl sulphates, alkyl ammonium salts and castor oil ethoxylates to activate an organoclay stabiliser that is suitable for use with a low polarity liquid.

The present invention still further provides a method of controlling undesired weeds in a location, comprising applying to the weed or the location a physically stable oil dispersion, or a dilution thereof, containing a herbicide, in a herbicidally effective amount. A dilution may be prepared by adding the oil dispersion to further low polarity oil or to another low polarity oil with which the oil of the oil dispersion of miscible. The application of the oil dispersion may vary within wide limits and depends on the nature of the soil, the method of application (pre- or post-emergence; seed dressing; application to the seed furrow etc), the crop plant, the undesired vegetation to be controlled, the prevailing climatic conditions and other factors.

Suitably the location comprises a crop such as citrus fruit, grapevines, nuts, oil palm, olives, pome fruit, stone fruit, rubber, turfgrass, barley, wheat, cotton, oilseed rape, maize, rice, soy beans, sugar beet, sugar cane, sunflowers, ornamentals and vegetables. Suitably, the crop is turfgrass.

The weeds to be controlled may be both monocotyledonous species, for example *Agrostis, Alopecurus, Avena, Bromus, Cyperus, Digitaria, Echinochloa, Lolium, Medicargo, Monochoria, Poa, Rottboellia, Sagittaria, Scirpus, Setaria, Sida, Soliva* and *Sorghum*, and dicotyledonous species, for example *Abutilon, Amaranthus, Chenopodium, Chrysanthemum, Galium, Ipomoea, Nasturtium, Sinapis, Solanum, Stellaria, Trifolium, Veronica, Viola* and *Xanthium*.

When the pesticide in the oil dispersion is a sulfonylurea, the application rate of the active ingredient will typically be from 5 to 150 g/ha, more suitably from 10 to 100 g/ha.

EXAMPLES

Example 1

Preparation of Anti-Settling System Formulation

The low polarity liquid (57.4 g) was charged to a temperature-controlled vessel at ambient temperature and mixed under high shear using a rotor-stator mixer (for example, L4R model from Silverson), operating at 5000 rpm. An organoclay (1.0 g) was added while high shear was maintained, followed by optional propylene carbonate (0.1 g, if used), emulsifier (7.5 g) and optional glycol ether (2.0 g, if used), in that order. The temperature of the dispersion was maintained at from 20 to 25° C. and the high shear mixing increased to 7500 rpm and maintained at this rate for 15 minutes at this temperature. The degree of separation of the anti-settling system was visually assessed after storage for approximately 1 month at room temperature. Anti-settling system formulations 1A to 1AI prepared in this way are detailed in Table 1.

TABLE 1

| Anti-settling system Formulation | Organoclay | | | | Low polarity liquid | | | | | | |
|---|---|---|---|---|---|---|---|---|---|---|---|
| | Bentone 34 | Bentone 38 | Bentone 120 | Bentone lt | Sunspray 11N | Isopar V | Isopar M | Solvesso 200 ND | Methylated rape seed oil | Dipropylene glycol dibenzoate | Oleic acid |
| 1A | | x | | | x | | | | | | |
| 1B | | x | | | x | | | | | | |
| 1C | | x | | | x | | | | | | |
| 1D | | x | | | x | | | | | | |
| 1E | | x | | | x | | | | | | |
| 1F | | x | | | x | | | | | | |
| 1G | x | | | | x | | | | | | |
| 1H | x | | | | x | | | | | | |
| 1I | | | x | | x | | | | | | |
| 1K | | | x | | x | | | | | | |
| 1L | | | | x | x | | | | | | |
| 1M | | | | x | x | | | | | | |
| 1N | | x | | | | x | | | | | |
| 1O | | x | | | | x | | | | | |
| 1P | | x | | | | | x | | | | |
| 1Q | | x | | | | | x | | | | |
| 1R | | x | | | | | x | | | | |
| 1S | | x | | | | | | x | | | |
| 1T | | x | | | | | | x | | | |
| 1U | | x | | | | | | | x | | |
| 1V | | x | | | | | | | | x | |
| 1W | | x | | | | | | | | | x |
| 1X | | x | | | x | | | | | | |
| 1Y | | x | | | x | | | | | | |
| 1Z | | x | | | x | | | | | | |
| 1AA | | x | | | x | | | | | | |
| 1AB | | x | | | x | | | | | | |
| 1AC | | x | | | x | | | | | | |
| 1AD | | x | | | x | | | | | | |
| 1AE | | x | | | x | | | | | | |
| 1AF | | x | | | x | | | | | | |
| 1AG | | x | | | x | | | | | | |
| 1AH | | x | | | x | | | | | | |
| 1AI | | x | | | x | | | | | | |

TABLE 1-continued

| Formulation | Anti-settling system Emulsogen M | Emulsifier Sunaptol CA350 | Rhodafac RS610 | Empicool LZ | Arquad 16-50 | Other Propylene carbonate | Propylene glycol monobutyl | Separation after 1 mo at RT (%) |
|---|---|---|---|---|---|---|---|---|
| 1A |  |  |  |  |  | x |  | >95 |
| 1B | x |  |  |  |  |  |  | <5 |
| 1C | x |  |  |  |  | x |  | <5 |
| 1D | x |  |  |  |  | x | x | <5 |
| 1E | x |  |  |  |  |  | x | <5 |
| 1F |  |  |  |  |  |  |  | >95 |
| 1G | x |  |  |  |  |  |  | 17 |
| 1H | x |  |  |  |  | x |  | <5 |
| 1I | x |  |  |  |  |  |  | 48 |
| 1K | x |  |  |  |  | x |  | <5 |
| 1L | x |  |  |  |  |  |  | >95 |
| 1M | x |  |  |  |  | x |  | >95 |
| 1N | x |  |  |  |  |  |  | <5 |
| 1O | x |  |  |  |  | x |  | <5 |
| 1P | x |  |  |  |  |  |  | 10 |
| 1Q | x |  |  |  |  | x |  | 25 |
| 1R | x |  |  |  |  | x | x | 10 |
| 1S | x |  |  |  |  |  |  | >95 |
| 1T | x |  |  |  |  | x |  | >95 |
| 1U | x |  |  |  |  | x | x | >95 |
| 1V | x |  |  |  |  | x | x | >95 |
| 1W | x |  |  |  |  | x | x | >95 |
| 1X |  | x |  |  |  |  |  | 60 |
| 1Y |  | x |  |  |  |  |  | 40 |
| 1Z |  | x |  |  |  | x | x | 20 |
| 1AA |  |  | x |  |  |  |  | 40 |
| 1AB |  |  | x |  |  | x |  | 5 |
| 1AC |  |  | x |  |  | x | x | <5 |
| 1AD |  |  |  | x |  |  |  | 35 |
| 1AE |  |  |  | x |  | x |  | 10 |
| 1AF |  |  |  | x |  | x | x | <5 |
| 1AG |  |  |  |  | x |  |  | 60 |
| 1AH |  |  |  |  |  | x | x | 50 |
| 1AI |  |  |  |  | x | x | x | 5 |

The results show that organoclays that are suitable for use with low polarity oils can be effectively activated by various emulsifiers, as reflected in the low percentage separation of the resulting anti-settling systems after storage for 1 month.

Example 2

Preparation of Anti-Settling System Concentrate

Anti-settling system concentrates 2A to 2F were prepared in the same manner as anti-settling system formulation 1D, but using reduced amounts of mineral oil to give final concentrations of Bentone 38™ as indicated in Table 2.

TABLE 2

| Anti-settling system concentrate | Bentone 38 concentration (% w/w) | Separation after 1 month at RT (%) |
|---|---|---|
| 2A | 1.5 | <5 |
| 2B | 2.0 | <5 |
| 2C | 2.2 | <5 |
| 2D | 3.0 | <5 |
| 2E | 3.3 | <5 |
| 2F | 4.0 | <5 |

The results show that increasing the concentration of organoclay up to 4.0% w/w does not affect the stability of the anti-settling system.

Example 3

Preparation of Oil Dispersion Formulations

Oil Dispersion 3.1

Anti-settling system formulation 1D was charged to a temperature-controlled vessel and stirred at 25° C. using conditions to achieve good bulk mixing. Propylene glycol monobutyl ether (2.0 g) was added whilst stirring was maintained. A finely ground (to a particle size of from about 1 to about 10 µm) 40% w/w suspension of trifloxysulfuron (as sodium salt) in Sunspray™ 11N, prepared separately, was added to give a final concentration of 100 g/l and bulk mixing was maintained until the preparation was visually homogeneous. This formulation was found to exhibit <5% separation after 1 year storage at 25° C., or after 8 weeks at 40° C., or after 2 weeks at 54° C. These results show that the resulting oil dispersion has long term physically stability.

Oil Dispersions 3.2-3.6

An equivalent oil dispersion to example 3.1 was prepared from each of anti-settling system concentrates 2A-2F. In each case, the balance of mineral oil required to achieve the target trifloxysulfuron concentration was charged initially to the vessel, followed by the anti-settling system concentrate, followed by the finely ground (to a particle size of from about 1 to about 10 µm) 40% w/w suspension of trifloxysulfuron (as sodium salt) in Sunspray™ 11N, with bulk mixing maintained until the mixture was visually homogeneous. (No additional glycol ether was added in this example as this was already included in the anti-settling system concentrates.) These formulations were all found to exhibit <5% separation after 2 weeks at 54° C. These results show that long term physical stability is also observed with oil dispersions made using elevated levels of organoclay stabiliser.

Oil Dispersions 3.7-3.10

Equivalent oil dispersions to example 3.1 were prepared using a variety of glycol ethers. The resulting stability data is shown in Table 3.

TABLE 3

| Oil Dispersion | Glycol Ether | Separation after 2 weeks at 54° C. (%) |
|---|---|---|
| 3.1 | Propylene glycol butyl ether | <5 |
| 3.7 | Butoxyethanol | 6 |
| 3.8 | Diethylene glycol monoethyl ether | 5 |
| 3.9 | Diethylene glycol monobutyl ether | <5 |
| 3.10 | Propylene glycol methyl ether | 5 |

The results demonstrate that good physical stability can be achieved when using various different glycol ethers in conjunction with the present invention.

Oil Dispersions 3.11-3.14

Equivalent oil dispersions to example 3.1 were prepared varying the amount of glycol ether (propylene glycol monobutyl ether) and emulsifier (Emulsogen M) present. The resulting stability data is shown in Table 4.

TABLE 4

| Oil Dispersion | Glycol ether (parts) | Emulsifier (parts) | Organoclay (parts) | Separation after 2 wks at 54° C. (%) |
|---|---|---|---|---|
| 3.1 | 2 | 7.5 | 1 | <5 |
| 3.11 | 0 | 9.5 | 1 | <5 |
| 3.12 | 4.5 | 5 | 1 | <5 |
| 3.13 | 7.5 | 2 | 1 | <5 |
| 3.14 | 9.5 | 0 | 1 | 24 |

The results show that good physical stability is achieved when the oil dispersion is prepared using differing amounts of emulsifier and glycol ether, but that at least some emulsifier is needed to provide excellent physical stability of the oil dispersion.

Oil Dispersions 3.15-3.17

Equivalent oil dispersions to example 3.1 were prepared using anti-settling systems 1B, 1E & 1F in place of 1D. In each case the low-shear rheological behaviour of the oil dispersion was measured using a UDS200 rheometer (Paar Physica) with cone-and-plate geometry. The elastic modulus (G') and cohesive energy (Em) measured for these samples are summarised in Table 5.

TABLE 5

| Oil Dispersion | Anti-settling system | G' (Pa) | Em (mJ/m$^3$) | Separation after 2 wks at 54° C. (%) |
|---|---|---|---|---|
| 3.1 | 1D | 73.8 | 33.2 | <5 |
| 3.15 | 1E | 44.6 | 57.1 | <5 |
| 3.16 | 1B | 16.1 | 27.6 | <5 |
| 3.17 | 1F | 1.3 | 6.7 | >95 |

Example 4

Preparation of Anti-Settling System Formulation at Different Temperatures

A series of anti-settling systems were prepared to a similar recipe as that used in example 1D, using a saw-tooth mixer to disperse the organoclay. The temperature at which the preparation was carried out was varied across the series. The separation data are shown in Table 6.

TABLE 6

| Anti-settling system | Temperature during preparation | Separation after 2 wks at 54° C. (%) |
|---|---|---|
| 4A | 5 | 76 |
| 4B | 10 | 69 |
| 4C | 12.5 | 64 |
| 4D | 15 | 58 |
| 4E | 17.5 | 13 |
| 4F | 20 | 7 |
| 4G | 22.5 | <5 |
| 4H | 25 | 6 |

The results show that the higher the temperature at which the formulation is prepared, the better the physical stability of the oil dispersion.

The invention claimed is:

1. A physically stable oil dispersion comprising:
   a) an organoclay stabiliser selected from the group consisting of tetraalkyl ammonium bentonite, tetraalkyl ammonium hectorite and tetra(alkyl/aryl)ammonium bentonite,
   b) an alkyl ethoxylate emulsifier,
   c) a low polarity liquid selected from the group consisting of paraffinic oil and mineral oil having a dielectric constant less than 2.5, and
   d) an oil insoluble pesticide that has a particle size of from about 1 to about 10 μm and is substantially insoluble in the low polarity liquid,
   wherein the organoclay stabiliser is activated by a method comprising mixing the organoclay stabiliser with the alkyl ethoxylate emulsifier under high shear conditions in the presence of the low polarity liquid at a temperature above 15° C. wherein the ratio range of the organoclay to the emulsifier ranges from about 1:10 to about 1:1.

2. A physically stable oil dispersion according to claim 1, further comprising a polar activator present in an amount up to 20% w/w compared to the organoclay stabiliser.

3. A physically stable oil dispersion according to claim 2, wherein the oil dispersion contains less than 20% w/w polar activator compared to the organoclay stabiliser.

4. A physically stable oil dispersion according to claim 1, further comprising a glycol ether.

5. A physically stable oil dispersion according to claim 1, wherein the oil insoluble pesticide is selected from the group consisting of ALS inhibitors, HPPD inhibitors, neonicotinoids, carbamates, avermectins, pyrethroids, bisamides, triazoles, mandelamides and strobilurins.

6. A physically stable oil dispersion according to claim 2, wherein the organoclay stabiliser is tetraalkyl ammonium hectorite, the low polarity liquid is mineral oil and the polar activator is propylene carbonate.

* * * * *